US005518882A

United States Patent [19]
Lund et al.

[11] Patent Number: 5,518,882
[45] Date of Patent: May 21, 1996

[54] IMMUNOLOGICAL METHODS OF COMPONENT SELECTION AND RECOVERY

[75] Inventors: Garry Lund, Edmonton; Thomas Wegmann, deceased, late of Edmonton, by Brenda Wegmann, executor; Timothy Mosmann, Edmonton, all of Canada

[73] Assignee: Biotex Laboratories, Inc., Edmonton, Canada

[21] Appl. No.: 172,133

[22] Filed: Dec. 21, 1993

[51] Int. Cl.$^6$ .................................................. G01N 33/53
[52] U.S. Cl. .......................... 435/6; 435/7.21; 435/7.5; 435/7.8; 435/7.93; 436/501; 436/518; 436/541; 436/543
[58] Field of Search ........................... 435/6, 7.21, 7.5, 435/7.8, 7.93, 969, 975; 436/518, 501, 541, 543

[56] References Cited

U.S. PATENT DOCUMENTS

| | | | |
|---|---|---|---|
| 4,228,237 | 10/1980 | Hevey et al. | 435/5 |
| 4,253,996 | 3/1981 | Katz | 525/54.1 |
| 4,276,206 | 6/1981 | Katz | 525/54.1 |
| 4,298,685 | 11/1981 | Parikh et al. | 435/7.5 |
| 4,468,470 | 8/1984 | Aalberse | 436/539 |
| 4,496,654 | 1/1985 | Katz et al. | 435/7.5 |
| 4,778,751 | 10/1988 | El Shami et al. | 435/7.92 |
| 4,814,434 | 3/1989 | Goldfarb | 530/380 |
| 5,078,673 | 1/1992 | Abrams | 600/3 |
| 5,116,724 | 5/1992 | Delaage et al. | 435/2 |
| 5,137,804 | 8/1992 | Greene et al. | 435/5 |
| 5,139,933 | 8/1992 | Green et al. | 435/7.32 |
| 5,153,166 | 10/1992 | Jain et al. | 530/811 |
| 5,215,927 | 6/1993 | Berenson et al. | 436/541 |

FOREIGN PATENT DOCUMENTS

| | | |
|---|---|---|
| 0325474 | 7/1989 | European Pat. Off. . |
| 87/04628 | 8/1987 | WIPO . |
| 92/16841 | 10/1992 | WIPO . |
| WO95/07466 | 3/1995 | WIPO . |

OTHER PUBLICATIONS

Braun and Kumel (1986) "Separation of T Cell Subpopulations by Monoclonal Antibodies and Affinity Chromatography" *Methods in Enzymology* 121:737–748.
Ghetie et al. (1978) "Separation of Cells by Affinity Chromatography on SpA–sepharose 6MB" *J. Immunol. Methods* 21:133–141.
Rubin (1976) "Regulation of Helper Cell Activity by Specifically Adsorbable T Lymhocytes" *J. Immunol.* 116:80–85.
Finn and Hofmann (1990) "Isolation and Characterization of Hormone Receptors" *Methods in Enzymology* 185:244–274.
Cassano (1989) "Murine Monoclonal anti–avidin antibodies enhance the sensitivity of avidin–biotin immunoassays and immunohistologic staining" *J. Immunol. Methods* 117:169–174.
Korenman and O'Malley (1970) "Newer Methods of Avidin Assay" *Methods in Enzymology* 18A:427–430.
Pharmacia (1986) "Affinity Chromatography" pp. 87–88, Rahms i Lund.
Basch et al., (1983), "Cell Separation Using Positive Immunoselective Techniques" *J. Immunol. Methods* 56:269–80.
Berenson et al., (1986) "Positive Selection of Viable Cell Populations using Avidin–biotin Immunoadsorption" *J. Immunol. Methods* 91:11–19.
Berman and Basch, (1980) "Amplification of the biotin–avidin immunofluorescence technique" *J. Immunol. Methods* 36:335–338.

(List continued on next page.)

*Primary Examiner*—Toni R. Scheiner
*Attorney, Agent, or Firm*—Burns, Doane, Swecker & Mathis; Gerald F. Swiss; Leslie A. Mooi

[57] ABSTRACT

The invention involves an immunological method of separating specifically-targeted cells or molecular structures from a mixed population under conditions which minimize damage to the cellular structure or the molecular integrity. The method is based upon the specific interaction of a label and an antibody directed against the label and the ability of a competitor to inhibit the interaction between the label and the antibody.

20 Claims, 3 Drawing Sheets

OTHER PUBLICATIONS

Clark et al., (1982) "Positive and Negative Selection of Cells by Hapten Modified Antibodies" *J. Immunol. Methods* 51:167–170.

Goetzel and Metzger, (1970) "Affinity Labeling of a Mouse Myeloma Protein which binds Nitrophenyl Ligands. Kinetics of Labelling and Isolation of a Labeled Peptide" *Biochemistry* 9:1267–1278.

Hoffman et al. (1977) "Biotinylinsulins as Potential Tools for Receptor Studies" *Proc. Natl. Acad. Sci. USA* 74:2697–2700.

Jasiewicz et al., (1976) "Selective Retrieval of Biotin–labeled Cells using Immobilized Avidin" *Exp. Cell Res.* 100:213–19.

O'Shannessy, D. J. and Hofmann, W. L. (1987) "Site–directed Immobilization of Glycoproteins on Hydrazide–containing Solid supports" *Biotech. Appl. Biochem.* 9:488–496.

Prud'homme et al., (1984) "Immune Dysfunction in Diabetes–prone BB Rats" *J. Exp. Med.* 159:463–478.

Scott, (1976) "Antifluorescein Affinity Columns" *J. Experimental Med.* 144:69–78.

Tizard, Ed, *Immunology: An Introduction*, (1984) Saunders College Publishing, pp. 108–111.

Vogt, R. F. et al., (1987) "Quantitative Differences Among Various Proteins as Blocking Agents for ELISA Microtiter Plates" *J. Immunol. Methods* 101:43–50.

Weetall H. (1976) "Covalent Coupling Methods for Inorganic Support Materials" *Meth. in Enzymol.* 44:134–148.

Wormmeester et al., (1984) "A Simple Method for Immunoselective Cell Separation with the Avidin–Biotin System" *J. Immunol. Methods* 67:389–94.

Abbas, A. K. et al. Cellular and Molecular Immunology Philadelphia: W. B. Saunders, 1991. pp. 53–55.

Harmon, F. "Purification of antibodies against biotinon lipoic acid–sepharose." Analytical Biochemistry 103:58–63, 1980.

Johnson, A. H. et al. "Affinity chromatographed with anti-–fluorescein antibody to separate Ig–positive cells: preliminary report." Transplantation Proceedings 9(1): 145–146, 1977.

Steinitz, M. et al. "Separation of rare subpopulations with the aid of biotin–labelled ligands." Medical Oncology and Tumor Pharmacotherapy 10(1/2): 49–52, 1992.

Wilchek, M. et al. "The Avidin–Biotin Complex in Bioanalytical Applications". Analytical Biochemistry 171: 1–32, 1988.

IMMUNOLOGICAL METHODS OF COMPONENT SELECTION AND RECOVERY

FIELD OF THE INVENTION

The present invention involves a method of separating and recovering specifically-targeted cells or molecular structures from mixed cell or molecular structure populations using antibodies.

REFERENCES

The following references are cited in the application and hereby incorporated by reference in their entirety.
1) U.S. Pat. No. 4,228,237;
2) U.S. Pat. No. 4,253,996;
3) U.S. Pat. No. 4,276,206;
4) U.S. Pat. No. 4,298,685;
5) U.S. Pat. No. 4,468,470;
6) U.S. Pat. No. 4,496,654;
7) U.S. Pat. No. 4,814,434;
8) U.S. Pat. No. 5,078,673;
9) U.S. Pat. No. 5,116,724;
10) U.S. Pat. No. 5,139,933;
11) U.S. Pat. No. 5,215,927;
12) International Patent Application No. WO 87/04628;
13) International Patent Application No. WO 92/16841;
14) European Patent Application No. 0 325 474;
15) Basch et al., (1983) "Cell Separation Using Positive Immunoselective Techniques" *J. Immunol. Methods* 56:269–80;
16) Berenson et al., (1986) "Positive Selection of Viable Cell Populations using Avidin-biotin Immunoadsorption" *J. Immunol. Methods* 91:11–19;
17) Berman and Basch, (1980) "Amplification of the biotin-avidin immunofluorescence technique" *J. Immunol. Methods* 36:335–338;
18) Clark et al., (1982) "Positive and Negative Selection of Cells by Hapten Modified Antibodies" *J. Immunol. Methods* 51:167–170;
19) Forsgren et al. (1977) *J. Immunol.* 99:19;
20) Goetzel and Metzger, (1970) "Affinity Labelling of a Mouse Myeloma Protein which binds Nitrophenyl Ligands. Kinetics of Labelling and Isolation of a Labeled Peptide" *Biochemistry* 9:1267–1278;
21) Hoffman et al. (1977) *Proc. Natl. Acad. Sci. USA* 74:2697–2700;
22) Jasiewicz et al., "Selective Retrieval of Biotin-labeled Cells using Immobilized Avidin" *Exp. Cell Res.* 100:213–19;
23) O'Shannessy, D. J. and Hofmann, W. L. (1987) *Biotech. Appl. Biochem.* 9:488;
24) Prud'homme et al., (1984) "Immune Dysfunction in Diabetes-prone BB Rats" *J. Exp. Med.* 159:463–78;
25) Tizard, Ed, *Immunology: An Introduction,* (1984) Saunders College Publishing;
26) Vogt, R. F. et al., (1987) *J. Immunol. Methods* 101:43;
27) Scott, (1976) "Antifluorescein Affinity Columns" *J. Experimental Med.* 144: 69–78;
28) Weetall H. (1976) *Meth. in Enzymol.* 44:134–148; and
29) Wormmeester et al., (1984) "A Simple Method for Immunoselective Cell Separation with the Avidin-Biotin System" *J. Immunol. Methods* 67:389–94.

BACKGROUND OF THE INVENTION

There is a need to recover certain cell types or certain molecular structures from mixed populations of cells or molecular structures.

Immunoselection is a generic term which encompasses a variety of techniques for the separation of cells or molecular structures bearing function related or lineage specific antigenic determinants. The specificity of the selection process is conferred by antibody or antibody-like molecules, haptens or lectins which interact with the specific cell surface or molecular structure antigenic determinants.

In recent years the biotin-avidin system has been applied to a variety of analytical and preparative procedures and has found wide spread use in immunoselection techniques for cell separation.

In general, two types of immunoselection techniques are available. "Negative selection" involves the removal of a specific subpopulation of cells from a heterogenous mixture of cell types. Using this method of separation, one can obtain an enriched but not pure preparation of remaining cells since all cell types in the original mixture that are negative for the selection antigen will be recovered. The second method, "positive selection" involves the specific targeting and recovery of cells expressing the desired specificity from a heterogenous population of contaminating cells. Positive selection techniques can provide a highly enriched or even pure population of the desired antigen-positive cells, in contrast to negative selection methods in which all cell types that are target antigen-negative will be recovered.

Biotinylated antibodies against rat thymocytes have been used to remove such thymocytes from a cell mixture by interaction with avidin covalently coupled to nylon meshes but removal of the thymocyte cells from the avidin was not attempted (Jasiewicz et al., *Exp. Cell Res.* 100:213–19, 1976).

T cells have been removed from spleen cell preparations by reaction with biotinylated monoclonal antibody directed against T cell antigen followed by panning on avidin, coated plates but the T cells were not removed from the plates (Prud'homme et al., *J. Exp. Med.* 159:463–78, 1984). U.S. Pat. No. 4,298,685 also describes a negative selection process using biotin-avidin.

Biotinylated monoclonal antibodies have been used in combination with avidin coated sheep erythrocytes to form rosettes of selected cells which are then separated on density gradients (Wormmeester et al., *J. Immunol. Methods* 67:389–94, 1984). This procedure reportedly allows for both positive and negative selection of cell populations. However, positively-selected cells are coated with sheep erythrocytes which could affect their activity.

All of the described methods rely upon the direct interaction of biotin with avidin or streptavidin bound to a solid support matrix during the immunoselection process to achieve cell separation, whether by a process of positive or negative selection. However, because of the very high affinity of the biotin-avidin interaction, the process is essentially irreversible and it is difficult to recover intact, functional cell populations away from the solid support matrix.

Various attempts have been made to circumvent this difficulty including the use of biotin analogues with lower affinity for avidin (Basch et al., *J. Immunol. Methods* 56:269–80, 1983) or the use of avidin-Sepharose matrices with reduced affinity for biotin (U.S. Pat. Nos. 4,253,996 and 4,276,206). These methods reportedly yield an operable avidin/biotin based positive selection procedure. However, the efficiency of isolating the desired components is variable.

Additional antibody layers on targeted cells have also been used such that the linkage to the cell can be mechanically disrupted at the lower affinity antigen-antibody interaction site (Berenson et al., *J. Immunol. Methods* 91:11–19, 1986; U.S. Pat. No. 5,215,927; International Patent No. WO 87/04628). This process, however, does not allow for the specific elution of the selected, retained cell population since any contaminating cells non-specifically adsorbed to or mechanically trapped by the avidin-derivatized solid phase may also be released by the mechanical agitation elution process. Further the mechanical agitation process may damage the cells.

International Patent Application Publication No. WO 92/16841 discloses a non-immune, reversible binding displacement system for the detection of compounds in a solution. Specifically, the application discloses the attachment of a releasable ligand, a binding partner for the releasable ligand, an analyte of interest, an analytically detectable (reporter) group and at least one binding partner for the analyte to an insoluble phase. A displacer ligand is added to the solution which displaces the releasable ligand along with some portion of the reporter-labeled complex which may or may not contain the analyte of interest so as to detect the presence of the analyte. This method discloses the use of biotin analogues with lower affinity for avidin as the releasable ligand.

Both positive and negative immunoselection methods for cell or molecular structure separation would be improved by a procedure which allowed for a high degree of specificity and selectivity in targeting of cells and provided for an efficient means of recovering those targeted cells from the solid support under conditions which minimized damage to the cellular structure and/or molecular integrity.

SUMMARY OF THE INVENTION

The present invention involves a method of separating and recovering specifically-targeted cells or structures from mixed cell or molecular structure populations under conditions which minimize damage to the cellular structure and/or the molecular structure and integrity. The method is based upon the specific interaction of a label and an antibody directed against the label and the ability of a competing ligand to compete with the interaction between the label and the antibody. The method employs a labelled binding molecule specific for a target molecule or epitope on a cell or structure, an antibody attached to a solid support which reacts with the label on the binding molecule to select the specific cell or structure and a competitor to the label-antibody interaction to release the cell or structure from the solid support.

One aspect of the invention is a method of selection and recovery of components from a mixed population wherein the desired components are attached to a labeled molecule which labeled molecule is bound to an anti-label antibody attached to a solid support and wherein the label is avidin, streptavidin or biotin comprising:

(a) reacting said solid support-antibody-label-component complexes with competitor wherein the competitor comprises biotin if the label is avidin or streptavidin and the competitor comprises avidin or streptavidin if the label is biotin, under conditions to allow the component-binding molecule-label complexes to be released from the solid support; and (b) recovering the component-label complexes.

Another aspect of the invention is a method of selection and recovery of components from a mixed population comprising:

(a) reacting a suspension of the components with a suspension of labelled binding molecules which binding molecules are complementary to the selected components wherein the label is selected from the group consisting of avidin, streptavidin and biotin, under conditions which allow the labelled binding molecules to bind to certain components and form component-binding molecule-label complexes;

(b) removing the excess labelled binding molecules;

(c) contacting said component-binding molecule-label complexes with a solid support comprising anti-label antibodies attached to said support wherein the antibodies are capable of binding to the label, under conditions to allow the component-binding molecule-label complexes to bind to the antibodies to form solid support-antibody-label-binding molecule-component complexes;

(d) recovering the solid support-antibody-label-binding molecule-component complexes;

(e) reacting said recovered solid support-antibody-label-binding molecule-component complexes with competitor wherein the competitor comprises biotin if the label is avidin or streptavidin and the competitor comprises avidin or streptavidin if the label is biotin, under conditions to allow the component-binding molecule-label complexes to be released from the solid support; and (f) recovering the component-binding molecule-label complexes.

Another aspect of the invention is a kit for the selection and recovery of components from a mixed population, comprising:

(a) labelled anti-component antibody wherein the label comprises avidin, streptavidin or biotin;

(b) anti-label antibody bound to a solid support; and (c) competitor, wherein the competitor is biotin if the label is avidin or streptavidin and the competitor is avidin or streptavidin if the label is biotin.

DETAILED DESCRIPTION OF THE INVENTION

Figure 1:
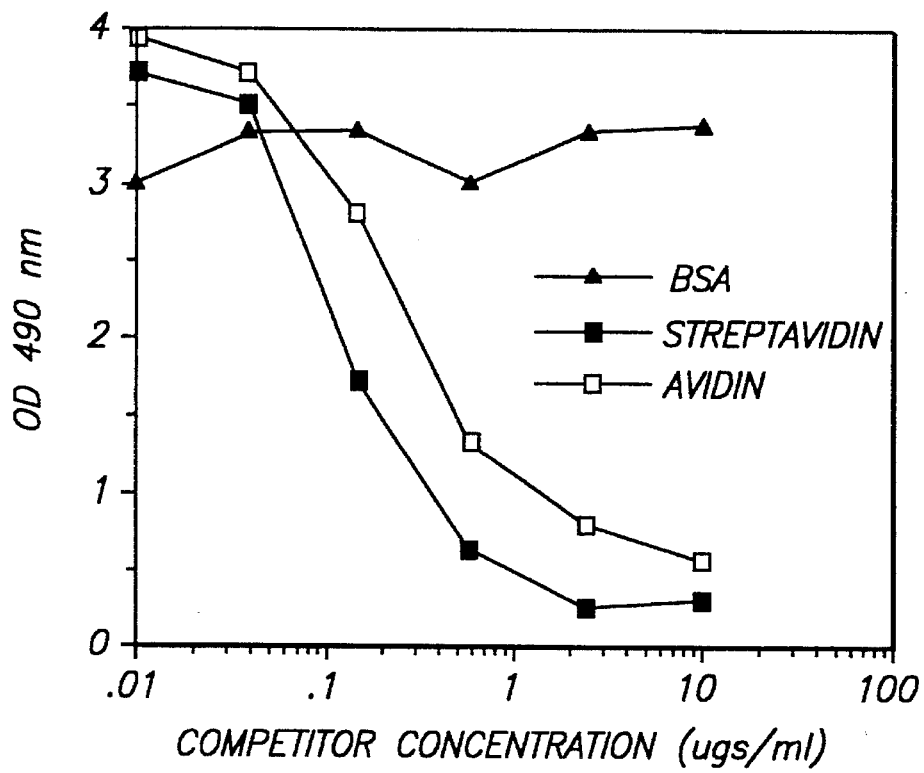
FIG. 1 illustrates the ability of avidin or streptavidin to inhibit the interaction between biotin and an antibody directed against biotin.

Briefly, the present invention involves a method of separating specifically-targeted cell or molecular structures from mixed cells or molecular structure populations under mild conditions which minimize damage to cellular structures and/or molecular integrity. The method is based upon the differing binding affinities of an anti-label antibody to a labeled component, and that of a competing molecule to the label. The method employs a labelled binding molecule specific for a target molecule or epitope on a cell or structure, an antibody which reacts with the label on the binding molecule and a competing molecule as an inhibitor of the binding molecule-label-antibody interaction.

Definitions

Before discussing the methodology of the present invention, the following terms will be defined.

The general term "immunoselection" as applied to cell separation describes a number of related techniques for separation of cells bearing function related or lineage specific antigenic determinants. The specificity of the selection process for cell separation can be conferred by antibody or antibody-like molecules, haptens or lectins which interact with specific cell surface antigens or markers.

The "components" can be cells, peptides, sub-cellular particles, oligosaccharides, or nucleic acids.

The "cells" can be bacterial cells, animal cells or vegetable cells and cells obtained by genetic recombination. The term also applies to other microorganisms and viruses.

The "mixed population" is any group of components containing a number of different component types. For example, the mixed population can be cells of bone marrow, blood, lymph nodes, spleen, liver or other tissues and organs. Alternatively, the mixed population can be a mixture of nucleic acids.

The "target molecule" or "epitope" is a molecule present on the cell which can be recognized by or bound with the "binding molecule". The "target molecule" being selected will depend on the cell population to be selected for, or against. The target molecule may be antigen (binds to antibody); antibody (binds to antigen); glycoconjugate (binds to lectin); lectin (binds to glycoconjugate); substrates, cofactors, inhibitors, etc. (binds with enzymes); hormones, effectors, toxins, etc. (binds with receptors); vitamins, amino acids, sugars, etc. (binds with transport proteins); hydrophobic sites (lipids or fatty acids); membranes (liposomes) or nucleic acids or genes recognized by DNA/RNA probes. In one embodiment, the "target molecule" is the CD4 antigen which is bound by the anti-CD4 antibody.

The cells and/or molecular structures can be selected from the mixed population under conditions which minimize damage to the cellular structure and/or molecular integrity by the methods of this invention by exploiting differences in the specific affinity of certain molecules for each other. The specific binding affinity of the label to the competitor must be a high specific binding affinity in the order of at least about $K_a=10^{11}M^{-1}$. In a preferred embodiment, the label and competitor are biotin and avidin or streptavidin respectively which have a binding affinity of $K_a=10^{15} M^{-1}$. Alternatively the label may be avidin or streptavidin and the competitor may be biotin. The binding affinity of the antibody-label reaction is a weaker specific affinity than the affinity between the label and the competitor. Antibody-antigen reactions have such a weaker affinity interaction characteristic of typically $K_a=10^5$ to $10^{10}M^{-1}$. See *Immunology: An Introduction* (1984), Editor I. R. Tizard, Saunders College Publishing. This allows the competitor to compete with the binding of the labelled binding molecule to the anti-label antibody, releasing the component.

The binding affinity of the competitor to the label must be greater than the binding affinity of the anti-label antibody to the label. It is contemplated that the greater the ratio in binding affinity of the competitor to the label as compared to the binding affinity of the anti-label antibody to the label, the faster the reaction. Preferably the ratio of the binding affinity of the competitor for the label to the affinity of the anti-label antibody to the label is at least about $10^5M^{-1}$, more preferably the binding affinity is at least about $10^6M^{-1}$. One skilled in the art could readily determine the binding affinities of the molecules.

In a preferred embodiment, the high affinity constant $(K_a=10^{15}M^{-1})$ between the vitamin biotin and the egg-white protein avidin or the bacterial protein from *Streptomyces avidinni*, streptavidin is exploited.

The "binding molecule" is a molecule which is capable of recognizing and binding with the target molecule present on the surface of the desired cell or within the desired molecule. The binding molecule used will depend on the target molecule on the cell or structure to be selected. The binding molecule may be antibody (recognizing antigen target); antigen (recognizing antibody target); glycoconjugate (recognizing lectin); lectin (recognizing glycoconjugate); enzymes (binding substrates, cofactors, inhibitors, etc.); receptors (hormones, effectors, toxins, etc.); transport proteins (binding vitamins, amino acids, sugars, etc.); lipids or fatty acids (hydrophobic sites); liposomes (membranes) or DNA/RNA probes recognizing nucleic acids or genes. In one embodiment the binding molecule is anti-CD4 antibody which recognizes CD4 antigen on the cell surface.

A binding molecule which has high specific binding activity for a target molecule is said to be complementary to the target molecule.

The binding molecule is tagged with a "label". In a preferred embodiment, the label is either biotin, avidin or streptavidin. Where the label is biotin, the competitor is avidin or streptavidin. On the other hand, where the label is avidin or streptavidin, the competitor is biotin.

The binding molecule is labelled by methods known in the art. The biotin molecule is linked to amino or carbohydrate residues located on the binding molecule. Biotin and methods of biotinylation are known. See for example Hoffman et al. (1977) *Proc. Natl. Acad. Sci. USA* 74:2697–2700 or Berman and Basch, (1980) "Amplification of the biotin-avidin immunofluorescence technique" *J. Immunol. Meth.* 36:335–338, both of which are incorporated herein by reference in their entirety. Alternatively, the binding molecule may be indirectly labelled by reacting it with a second biotinylated reagent, selected because it has a specificity for the binding molecule. For example the second reagent may be a biotinylated antibody to the binding molecule. Similarly, avidin or streptavidin may be linked to the binding molecule by methods known in the art. The parameters of such linkage are substantially as described for biotin above.

The "anti-label antibody" is an antibody which is able to detect and bind to the label. The antibodies used in the methods of this invention may be polyclonal or monoclonal antibodies. Preferably the binding affinity of the antibody to the label is a $K_a$ of from $10^5M^{-1}$ to $10^{10}M^{-1}$, more preferably the affinity is a $K_a$ of at least about $10^6M^{-1}$ to $10^8 M^{-1}$.

The preparation of polyclonal antibodies is known in the art and many polyclonal antibodies are commercially available. The basic process for making polyclonal antibodies involves injecting an animal with an immunogenic substance. In one embodiment, the substance is biotin, avidin, or streptavidin. Generally the biotin, avidin or streptavidin is attached to an antigenic carrier so as to elicit an immune response. After a suitable time for antibody production, antibodies are collected and isolated from the animal.

The preparation of monoclonal antibodies is known in the art and the monoclonal antibodies described in this invention are publicly available. The basic process for making monoclonal antibodies involves injecting an animal, usually a mouse with an immunogenic substance. After suitable time for antibody production to the immunogen, the mouse is sacrificed. Cells are removed from the spleen and fused with myeloma cells. Hybridoma cells resulting from this fusion are able to reproduce in vitro, and each expresses genetic information for one specific antibody. The antibodies produced from one hybridoma clone thus will recognize a single antigenic determinant of the immunogen.

Cells cultured from individual hybridoma cells are screened for production of antibodies to a determinant on the target antigen. Those hybridomas positive for the target antigen are further screened to identify those having the appropriate affinity. The monoclonal antibodies used in the present invention will have an affinity to the target antigen of at least $10^5$–$10^{10}M^{-1}$ and preferably at least $10^6$–$10^8M^{-1}$. Monoclonal antibodies displaying all of these characteristics are then screened using actual assay conditions to determine if the assay condition alters the antibody binding characteristics or affinity, and to screen out those with cross-reactivity to possible contaminating antigens.

In a preferred embodiment the anti-label antibody is either an anti-biotin antibody, an anti-avidin antibody or anti-streptavidin antibody. Preferably, the anti-biotin antibody is monoclonal BN-34 (Sigma, St. Louis, Mo.). For example, the anti-avidin antibody is polyclonal antibody A5170 (Sigma, St. Louis, Mo.) and the anti-streptavidin antibody is antibody S6390 (Sigma, St. Louis, Mo.).

The "competitor" or "competing molecule" is a molecule which is able to compete with the anti-label antibody for binding with the labelled binding molecule. In a preferred embodiment, where the label is biotin and the anti-label antibody is anti-biotin antibody, the competitor is preferably avidin or streptavidin. Where the label is avidin and the anti-label antibody is anti-avidin antibody the competitor is preferably biotin. Finally, where the label is streptavidin and the anti-label antibody is anti-streptavidin antibody, the competitor is preferably biotin.

The "solid phase" is any solid support to which the anti-label antibody may be bound. For example, the solid support may be polyacrylamide beads, magnetic beads, polystyrene, polyurethane, agarose, collagen, gelatin, Sepharose, Sephadex, Sepharon, nylon, rayon or glass. Additionally, the solid phase may be animal erythrocytes in which case the isolated cells could be separated from the other cells by the rosetting procedure, known in the art. The solid support can take various forms, including fibers, mesh, microtiter plates or tubing and can be housed in other flow-through devices such as extracorporeal cartridges in systems for continuously removing selected components.

The components are "recovered" when they are substantially isolated from the mixed population. Further the desired components are no longer attached to the solid phase. The percentage of isolation will vary depending on the components to be isolated. Preferably, the recovered components comprise at least about 70% of the total components in the recovered population, more preferably the recovered components comprise at least about 80% of the total components.

Methodology

The present invention is based upon the interaction between the label and antibody directed against the label and the inhibition of this interaction by the competitor. In a preferred embodiment, the label is biotin which is attached to the binding molecule and the anti-label antibody is anti-biotin antibody and the competitor is avidin or streptavidin. In another preferred embodiment, the invention may be practiced by employing an avidin-labeled binding molecule and antibody directed against avidin (commercially available from Sigma, St. Louis Mo.) and biotin as the competitor to inhibit the interaction between the avidin and the anti-avidin antibody.

Briefly, the mixed component suspension is incubated with labelled binding molecules under conditions which allow the binding molecule to bind to the specific desired components. Excess labelled binding molecules are removed. The component suspension is then placed in contact with a solid support to which anti-label antibody has been bound under conditions which allow the anti-label antibody to bind to the remaining binding molecules. Unabsorbed components are washed away from the solid support. The recovery of component populations which react with the labelled binding molecule are amplified using the methods of this invention. The solid support with the absorbed Components is plaid in contact with a solution having the competing molecule. The competitor competes with the anti-label antibody for binding to the labeled binding molecule and the specific desired components are released from the solid support into the solution and can be recovered.

The methods of this invention are now discussed in more detail.

The desired component is chosen and the binding molecule and target molecule selected to allow the desired component to be selected from the general mixed population. As discussed above, the binding molecule and the target molecule can vary depending on the component desired. In one embodiment, the desired cell type is CD4 positive lymphocytes; the binding molecule is anti-CD4 antibody to which a label such as biotin has been covalently attached; and the target molecule is CD4.

It is contemplated that the desired component may also be labelled with a reporter molecule. Any reporter group which is analytically detectable and compatible with the selection assay of the present invention can be used in the methods of this invention. Examples of such reporter groups include but are not limited to: enzymes, fluorescent dyes, phosphorescent dyes, radioisotopes, and electron dense markers. Enzymes are preferred reporters. The reporter group can be attached using known methods.

The solid support is prepared such that it is capable of binding the anti-label antibody in a manner such that the anti-label antibody is oriented so that the "active site" or Fab portion of the anti-label antibody molecule is available to bind to the label on the binding molecule.. Methods to so bind antibodies to solid supports are well known in the art including the covalent and non-covalent attachment of the antibodies to the support.

In one embodiment anti-mouse IgG (Fc specific) antibodies are used to attach the monoclonal anti-biotin antibodies to the glass bead solid support. The anti-mouse IgG (Fc specific) antibodies are attached to the glass beads by physical adsorption. The excess anti-mouse IgG antibodies are removed and the glass beads are contacted with mouse anti-biotin antibody. The anti-mouse IgG antibody binds to the Fc portion of the mouse anti-biotin antibody such that the Fab portion of the mouse anti-biotin antibody is free.

Other materials such as protein A or protein G which also bind to the Fc region of antibody may be employed. Protein A is first attached to the solid support and the antibodies of choice are then bound to the Protein A (Forsgren et al. (1977)

*J. Immunol.*, 99:19). The method of attachment of Protein A to the solid support may proceed by any one of several process available through the literature (Weetall H. (1976) *Meth. in Enzymol.* 44:134–148). Protein A attaches to the Fc portion of IgG subclass antibodies, thus extending and presenting the Fab portion of these antibodies. The resulting correct orientation of the antibodies and extension away from the particles leads to a very effective interaction between the bound antibodies and their target.

Chemical procedures such as hydrazide coupling chemistry (Bio-Rad) which would specifically attach antibody directly to the solid support via the Fc region of the molecule may also be used and provide for covalent attachment. See O'Shannessy, D. J. and Hofmann, W. L. (1987) *Biotech. Appl. Biochem.* 9:488.

The solid support with the anti-label antibody attached may be treated with a blocking solution to reduce non-specific binding of components to the solid support by methods known in the art. See Vogt, R. F., et al. (1987). *J. Immunol. Methods* 101:43.

The binding molecule is labelled by methods known in the art. The biotin molecule is linked to amino or carbohydrate residues located on the binding molecule. Biotin and methods of biotinylation are known. See for example Hoffman et al. (1977) *Proc. Natl. Acad. Sci. USA* 74:2697–2700 or Berman and Basch, (1980) "Amplification of the biotin-avidin immunofluorescence technique" *J. Immunol. Meth.* 36:335–338, both of which are incorporated herein by reference in their entirety. Where the binding molecule is an antibody, biotin may be linked to antibody in a ratio from 1:1 to 1:100 (antibody:biotin). Preferably, biotin may be linked to an antibody in a ratio of 1:1 to 1:30. Similarly, avidin or streptavidin may be linked to the binding molecule by methods known in the art. The parameters of such linkage are substantially as described for biotin above including the use of a ratio of antibody: avidin of 1:1 to 1:100 and preferably 1:1 to 1:30.

The population from which the components are to be selected, in the form of a solution, is placed in contact with the labelled binding molecule complex and incubated for a sufficient period of time and under conditions sufficient to allow the components having the selected target molecule to bind to the binding molecule. The length of time can vary from 20 minutes to 1 hour, more preferably from 40 minutes to 1 hour. The concentration of the components will depend on the type of binding molecule employed in the invention and the system in use. As an example, however, for CD4 the concentration of components would be on the order of 5 µg of labelled antibody per $50 \times 10^6$ cells. A sufficient concentration of labelled binding molecule is added to the components such that the molecules are in excess. One skilled in the art could readily determine the conditions necessary to ensure that sufficient components having the target molecule are bound to the labelled binding molecule. After a sufficient period of incubation, the excess labelled binding molecule is removed. One skilled in the art would know how to remove the excess labelled binding molecules. For example, if the components are cells, the cells may be centrifuged away from the excess labelled binding molecules. Alternatively, the excess labelled binding molecules may be removed by passage through a size gradient or gel.

The labelled components are then placed into contact with the solid support-anti-label antibody complex and incubated for a sufficient period of time and under conditions sufficient to allow the component-binding molecule-label complexes to bind to the anti-label antibody on the solid support. The length of time can vary from 10 minutes to 60 minutes, more preferably from 10 minutes to 15 minutes. The conditions are preferably neutral pH and isotonic salt. After a sufficient period of time the component solution is removed from the solid support.

Those unabsorbed components will be components which lack the target molecule. The components absorbed to the solid support will be components having the target molecule. The solid support may be washed a number of times to remove the non-specifically bound molecules which lack the target molecule.

The solid support is then placed in contact with a solution having the competitor. The competitor is preferably added in a solution wherein the competitor is in a molar excess to ensure that most of the components are released from the solid support. The solution is preferably of a salt concentration and pH which is compatible with the components (i.e. it does not result in denaturation of the components). The length of time of the incubation is sufficient to allow most of the components to be released from the solid support. The length of time will vary with the type of label and competitor used and the specific binding affinity of the label and the competitor. One skilled in the art given this disclosure could readily determine the conditions required to ensure sufficient release of the components from the solid support. Preferably, the time of incubation is from 20 minutes to 1 hour, more preferably, the amount of time is 40 minutes to 1 hour. The temperature of the reaction will be that temperature which is compatible with maintaining the viability of the components to be selected. Preferably the temperature is from 20° C. to 42° C., more preferably from 25° C. to 37° C. By the methods of this invention, the components are removed from the solid support without significant agitation. Significant agitation means any agitation other than the small agitation caused by the movement of containers from one position to another.

Since the competitor has a greater affinity for the component-binding molecule complexes than the anti-label antibody on the support, it allows the release of the components. The components released from the solid support are recovered. It is contemplated that the components may be washed with buffer to remove any excess competitor.

It is further contemplated that if the binding molecule is an antibody, the labelled binding molecule may be removed from the desired component by methods known in the art. For example chaotropic agents and extremes of pH may be used. Alternatively, methods compatible with the components may be used. For example, if the components are cells, they may be incubated in culture for a sufficient period of time to allow the anti-component labeled antibodies to be shed into the solution.

It is anticipated that this invention can be applied to the specific targeting, separation or quantitation of cells, viruses, yeast and molds, bacteria and other microorganisms and structures as well as their component parts.

The methods of this invention can be used to positively select cells for use in therapeutic purposes. Immature populations of peripheral lymphocytes can be collected by the methods of this invention and grown in vitro until maturation in order to expand their population prior to autologous reinfusion into the patient. For example, lymphokine activated killer cells (LAK) for use in cancer therapy or AIDS therapy, suppressor lymphocytes for treating thyroid diseases, T4 lymphocytes for treating AIDS, certain subpopulations of lymphocytes for multiple sclerosis and certain macrophages for attacking cholesterol plaques could be obtained by the methods of this invention. The methods of this invention can also be employed as a sensitive assay for detecting cancer remission or metastases, by monitoring the numbers of tumor cells in a patient's bloodstream or bone marrow.

In order to further illustrate the present invention and advantages thereof, the following specific examples are given, it being understood that the same are intended Only as illustrative and in nowise limitative.

EXAMPLES

Example 1: Inhibition of Interaction between Biotin and an Anti-biotin Antibody by Avidin or Streptavidin This example illustrates the ability of avidin or streptavidin to inhibit the interaction between biotin and an antibody directed against biotin.

Bovine serum albumin (BSA) (Sigma Chemical Company, St. Louis Mo.) was biotinylated with N-hydroxysuccinimidobiotin (Pierce Chemical Company, Rockford, Ill.) using standard procedures (See Berman and Basch (1980) *J. Immunol. Methods* 36:335–338)).

BSA was dialyzed against 0.1M $NaHCO_3$ (no azide) at pH 8.2 to 8.6. The BSA concentration was adjusted to 1 mg/ml. N-hydroxysuccinimidobiotin (Pierce No. 20217) was dissolved in dimethyl sulfoxide (DMSO) to a concentration of 1 mg/ml. The bottle of N-hydroxysuccinimidobiotin was warmed to room temperature before weighing, to prevent condensation. 120 µl of the biotin succinimide ester mixture was added to 1 ml of the dialyzed BSA, mixed immediately, and incubated at room temperature for 4 hours in the dark. The mixture was then dialyzed against phosphate buffered saline (PBS) with azide overnight at room temperature to remove uncoupled biotin.

Phosphate buffered saline (PBS) is 32 g NaCl, 0.8 g KCl, 4.6 g $Na_2HPO_4$, 0.8 g $KH_2PO_4$ in 1 liter $H_2O$ (pH 7.2). PBST is PBS with 0.05% Tween 20 (Sigma Chemical Company, St. Louis, Mo.).

The resulting biotinylated BSA (B-BSA) was used to coat the polyvinylchloride wells of enzyme immunoassay plates (Fisher, Edmonton, AB). The B-BSA was bound to each well by adding approximately 100 µl of a 1:4000 dilution of the B-BSA Solution to each well. The plates were incubated at 4° C. temperature in a humid atmosphere for 16 hours (approximately overnight). The unbound B-BSA solution was removed by washing the wells with PBST. The wells were then filled with Blocking Buffer (20% fetal calf serum (FCS) [GibcoBRL, Burlington, Ontario, Canada] in PBS) and incubated at 37° C. temperature for 20 minutes. The Blocking Buffer was removed.

The wells coated with B-BSA were then incubated for 1 hour at 37° C. with 100 µls (1:8000 dilution) of mouse monoclonal anti-biotin antibody (monoclonal, BN- 34, Sigma, St. Louis, Mo.). The excess antibody was removed by washing the wells three times with PBST. Duplicate wells were incubated at 37° C. for 1 hour with increasing concentrations from 0.01 to 100 µg/ml of the competitors: avidin, streptavidin (Boehringer Mannheim, Indianapolis Ind.) or BSA, as a control, diluted in PBS.

The excess competitors were then removed by washing the wells three times with PBST to remove the competitor and any eluted anti-biotin antibody.

The relative amount of anti-biotin antibody remaining bound to the solid phase B-BSA was quantitated using horseradish peroxidase (HRP) conjugated anti-mouse IgG (Sigma Chemical Company, St Louis Mo.) in standard enzyme immunoassay (EIA) methods. Specifically, goat anti-mouse IgG-HRP was diluted to 1/5000 in PBST+1% BSA and 75 µls were added to each well. The wells were then allowed to incubate for 30 minutes at 37° C. temperature. The excess IgG-HRP was removed by washing 5 times with PBST. Finally, 100 µls of Substrate Buffer (1 mg/ml 2',2'-Azino-bis(3 -ethylbenz-thiazoline-6-sulfonic acid), 0.003% $H_2O_2$, 44 mM $Na_2HPO_4$, and 28 mM citric acid in distilled water) was added to each well, and allowed to incubate for 30 minutes at room temperature. Positive wells appear green. The OD reading was determined at 405–490 nm.

FIG. 1 shows that increasing concentrations of either avidin or streptavidin were able to effectively inhibit the interaction between biotin and the monoclonal anti-biotin antibody. The amount of antibody remaining bound to solid phase B-BSA as detected by standard EIA methods decreased to very low levels at concentrations of inhibitor approaching 10 µg/ml. Increasing concentrations of the BSA control had no effect on the biotin-antibody interaction.

Example 2: Effect of Time and Temperature on the Inhibition of the Biotin-antibody Interaction The effect of time and temperature of incubation of the competitor on the biotin-antibody interaction was examined at two concentration levels of avidin and streptavidin by the method disclosed in Example 1. The concentrations of avidin used were either 10 µg/ml or 50 µg/ml. The concentrations of streptavidin used were either 1.0 µg/ml or 5.0 µg/ml. The period of incubation of the avidin or streptavidin with the wells coated with B-BSA and treated with anti-biotin antibody varied from 0 to 60 minutes. The incubation was conducted at either room temperature or at 37° C.

Figure 2:
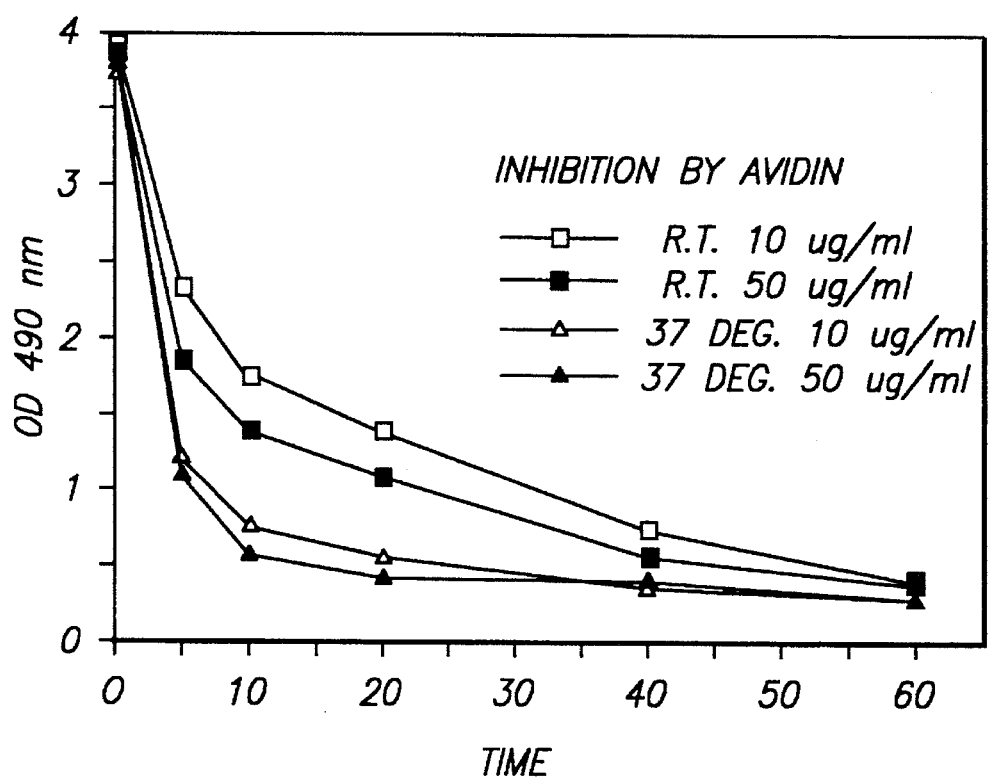
FIG. 2 illustrates the inhibition of the interaction between biotin and monoclonal anti-biotin antibody obtained with different concentrations of avidin at different temperatures.

FIG. 2 shows that there was no significant difference between the inhibition obtained with 10 µg/ml and 50 µg/ml concentrations of avidin. However, increasing the temperature of incubation with avidin from room temperature to 37° C. increased the initial rate at which antibody was eluted from the B-BSA coated wells. By 60 minutes the level of antibody remaining in the wells was the same, regardless of the incubation temperature or the concentration of avidin used.

Figure 3:
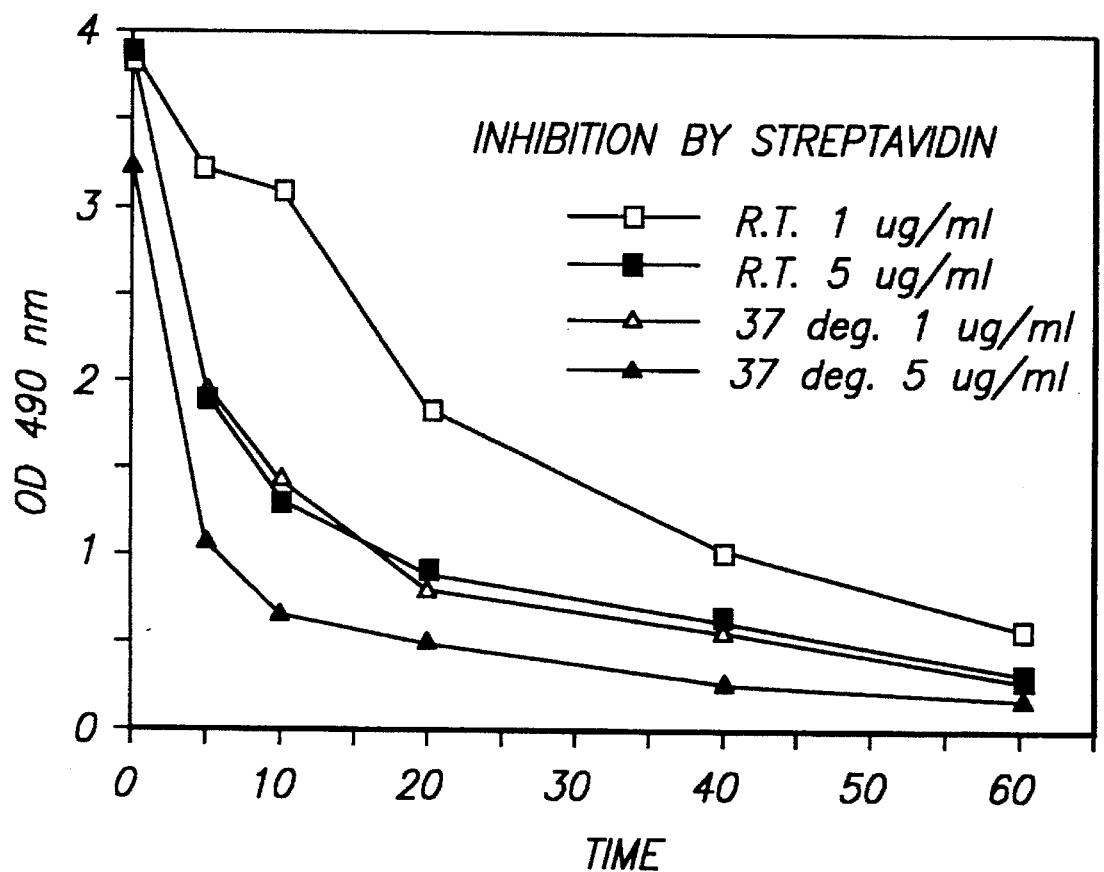
FIG. 3 illustrates the inhibition of the interaction between biotin and monoclonal anti-biotin antibody obtained with different concentrations of streptavidin at different temperatures.
Figure 4:
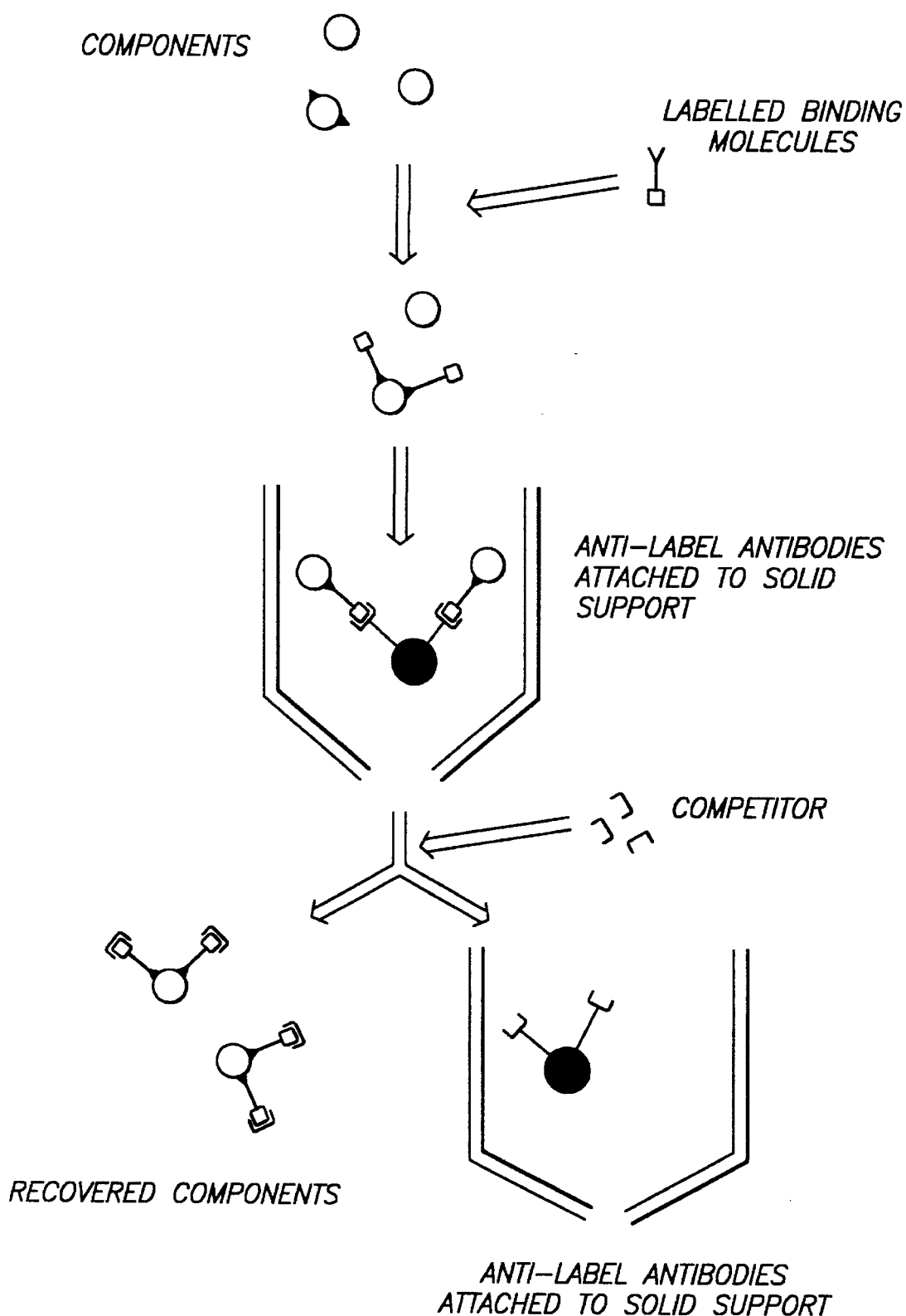
FIG. 4 illustrates a schematic diagram of a preferred embodiment of the immunoselection technique of the present invention.

The same experiment was performed with 1 µg/ml and 5 µg/ml of streptavidin (instead of avidin). The results are shown in FIG. 3. The 5 µg/ml concentration of streptavidin proved to be more effective than the 1 µg/ml concentration in competing with the antibody-biotin interaction, both at room temperature and at 37° C. For both concentrations of streptavidin, increasing the temperature of incubation also increased the rate at which antibody was eluted from the solid phase B-BSA. After 60 minutes of incubation, differences in concentration of the streptavidin or the temperature of incubation were no longer significant, similar to that observed with avidin.

It is anticipated that this invention can be applied to the specific targeting, separation or quantitation of cells, viruses, yeast and molds, bacteria and other microorganisms and structures as wells as their component parts.

Example 3: Separation of CD4 Lymphocytes from Human Peripheral Blood Lymphocyte Preparation In this Example, CD4 positive lymphocytes will be separated from human peripheral blood lymphocyte preparations. During this procedure, 5 μgs (for 50×10⁶ cells) of anti-human CD4 antibody (Pharmingen, San Diego, Calif., product no. 30151A) is biotinylated by the method described in Example 1. The biotinylated anti-human CD4 antibody is incubated with a lymphocyte preparation isolated from whole human blood using a Histopaque density gradient (Sigma Chemical Company, St. Louis, Mo.) for 1 hour at 4° C. temperature. The isolated cells are then washed with PBS twice to remove excess unbound antibody and loaded onto the following prepared column.

The column is composed of 2 ml glass beads, 80 to 100 mesh, to which goat IgG antibodies specific for the Fc portion of mouse IgG molecules are physically adsorbed by treating the beads with 0.15 mg/ml of goat IgG antibodies for 24 to 48 hours at 4° C. temperature. The beads are washed 5 times with PBS.

The beads thus coated are then incubated with 20 μl of the mouse monoclonal anti-biotin IgG antibodies (monoclonal, BN-34; Sigma, St. Louis, Mo.) per ml of beads. The antibodies are attached to the glass beads by interaction of their Fc portion with the anti-IgG goat antibodies, leaving the anti-biotin combining sites free to bind biotin. The beads are again washed with PBS and loaded into a 2 ml disposable polypropylene column (Isolab, Inc., Akron, Ohio).

The treated cell population contains CD4 positive cells coupled to biotin via their specific interaction with the targeting biotinylated anti-CD4 antibody, as described above. The 50×10⁶ cells are loaded in 1 ml onto the prepared column and are retained on the column matrix via the interaction between the solid phase anti-biotin antibody and the biotinylated CD4 antibody on the cell surface. The column is washed with five to six volumes of PBS+2% fetal calf serum to remove those cells lacking CD4. The positively selected CD4 cells are then eluted from the column by washing with PBS containing 5 μg/ml of streptavidin.

This same process may also be used to deplete a cell population of a specific cell type by the process of negative selection.

The described example uses anti-mouse IgG (Fc specific) antibodies to attach the monoclonal anti-biotin antibodies to the solid support but other materials such as protein A or protein G which also bind to the Fc region of antibody may be employed. Chemical procedures such as hydrazide coupling chemistry (Bio-Rad) which would specifically attach anti-biotin antibody directly to the solid support via the Fc region of the molecule may also be used.

While the invention has been described in terms of various preferred embodiments, the skilled artisan will appreciate that various modifications, substitutions, omissions and changes may be made without departing from the scope thereof. Accordingly, it is intended that the scope of the present invention be limited solely by the scope of the following claims, including equivalents thereof.

What is claimed is:

1. A method of selection and recovery of desired components from a mixed population wherein the desired components are specifically attached by their target molecule to a labelled binding molecule which labelled binding molecule is bound to an anti-label antibody attached to a solid support and wherein the label is avidin, streptavidin or biotin comprising:

(a) reacting said solid-support-antibody-labelled binding molecule-target molecule-component complexes with competitor wherein the competitor comprises biotin if the label is avidin or streptavidin and the competitor comprises avidin or streptavidin if the label is biotin, under conditions to allow the labelled binding molecule-target molecule-component complexes to be released from the solid support; and (b) recovering the labelled binding molecule-target molecule-component complexes.

2. The method according to claim 1 wherein the label is biotin and the antibody is anti-biotin antibody.

3. The method according to claim 2 wherein the competitor is avidin.

4. The method according to claim 2 wherein the competitor is streptavidin.

5. The method according to claim 1 wherein the label is avidin and the antibody is anti-avidin antibody.

6. The method according to claim 1 wherein the label is streptavidin and the antibody is anti-streptavidin antibody.

7. The method according to claim 5 wherein the competitor is biotin.

8. The method according to claim 5 wherein the competitor is biotin.

9. The method according to claim 1 wherein the components are cells.

10. The method according to claim 1 wherein the components are nucleic acids.

11. A method of selection and recovery of desired components from a mixed population comprising the steps of:

(a) reacting the mixed population of the components with a suspension of labelled binding molecules which binding molecules specifically bind a target molecule on the desired components wherein the label is selected from the group consisting of avidin, streptavidin and biotin under conditions which allow the labelled binding molecules to bind to the desired components and form component-binding molecule-label complexes;

(b) removing the excess labelled binding molecules;

(c) contacting said component-binding molecule-label complexes with a solid support comprising anti-label antibodies attached to said support under conditions to allow the component-binding molecule-label complexes to bind to the antibodies to form solid support-antibody-label-binding molecule-component complexes;

(d) recovering the solid-support-antibody-label-binding molecule-component complexes;

(e) reacting said recovered solid-antibody-label-binding molecule-component complexes with competitor wherein the competitor comprises biotin if the label is avidin or streptavidin and the competitor comprises avidin or streptavidin if the label is biotin, under conditions to allow the component-binding molecule-label complexes to be released from the solid support; and (f) recovering the component-binding molecule-label complexes.

12. The method according to claim 11 wherein the components are cells.

13. The method according to claim 11 wherein the label is biotin and the antibody is anti-biotin antibody.

14. The method according to claim 13 wherein the competitor is avidin.

15. The method according to claim 13 wherein the competitor is streptavidin.

16. The method according to claim 11 wherein the label is avidin and the antibody is anti-avidin antibody.

17. The method according to claim 11 wherein the label is streptavidin and the antibody is anti-streptavidin antibody.

18. The method according to claim 16 wherein the competitor is biotin.

19. The method according to claim 17 wherein the competitor is biotin.

20. A kit for the selection and recovery of components from a mixed population comprising:
(a) labelled anti-component antibody, wherein the label comprises biotin, avidin or streptavidin;
(b) anti-label antibody bound to a solid support; and
(c) competitor, wherein the competitor is biotin if the label is avidin or streptavidin and the competitor is avidin or streptavidin if the label is biotin.

* * * * *

UNITED STATES PATENT AND TRADEMARK OFFICE

CERTIFICATE OF CORRECTION

PATENT NO. : 5,518,882                    Page 1 of 3

DATED       : May 21, 1996

INVENTOR(S) : Garry Lund, Thomas Wegmann (deceased) by Brenda Wegmann, Executrix, Timothy Mosmann It is certified that an error appears in the above-identified patent and that said Letters Patent is hereby corrected as shown below:

Item [56]

At page 2, Other Publications, insert --Forsgren et al. (1967) "Protein A From Staphylococcus Aureus", *J. Immunol.* 99:19-24.--.

At column 1, line 40, replace "(1977)" with --(1967)--; and
    at line 47, after "Jasiewicz et al." insert --(1976)--.

At column 2, line 19, after ""positive selection"" insert --,--; and
    line 34, after "avidin" delete ",".

At column 7, line 6, replace "in vitro" with --*in vitro*--; and
    at line 36, after "anti-avidin antibody" insert --,--.

At column 8, line 21, replace "Components is plaid" with --components is placed--; and
    at line 51, delete second occurance of ".".

At column 11, line 8, replace "Only" with --only--.

At column 12, line 11, replace "(3 -ethylbenz-thiazoline-6-sulfonic acid)" with --(3-ethylbenz-thiazoline-6-sulfonic acid)--.

UNITED STATES PATENT AND TRADEMARK OFFICE

CERTIFICATE OF CORRECTION

PATENT NO. : 5,518,882

DATED : May 21, 1996

INVENTOR(S) : Garry Lund, Thomas Wegmann (deceased) by Brenda Wegmann, Executrix, Timothy Mosmann It is certified that an error appears in the above-identified patent and that said Letters Patent is hereby corrected as shown below:

```
At column 13, replace Claim 1 with the following:

1.   --A method of selection and recovery of desired
components from a mixed population wherein the desired
components are specifically attached by a target molecule
to a labelled binding molecule which labelled binding
molecule is bound to an anti-label antibody attached to a
solid support to form a solid-support-antibody-labelled
binding molecule-target molecule-component complex and
wherein the label is avidin, streptavidin or biotin
comprising:
        (a) reacting said solid-support-antibody-labelled
binding molecule-target molecule-component complexes with
competitor wherein the competitor comprises biotin if the
label is avidin or streptavidin and the competitior
comprises avidin or streptavidin if the label is biotin,
under conditions to allow the labelled binding molecule-
target molecule-component complexes to be released from
the solid support; and
        (b) recovering the labelled binding molecule-target
molecule-component complexes.--
```

UNITED STATES PATENT AND TRADEMARK OFFICE
CERTIFICATE OF CORRECTION

PATENT NO. : 5,518,882

DATED : May 21, 1996

INVENTOR(S) : Garry Lund, Thomas Wegmann (deceased) by Brenda Wegmann, Executrix, Timothy Mosmann It is certified that an error appears in the above-identified patent and that said Letters Patent is hereby corrected as shown below:

At column 14, Claim 8, delete "5" and insert --6--.

At column 14, Claim 11, step (e), lines 1 and 2 replace "solid-antibody-label-binding molecule-component complexes" with --solid-support-antibody-label-binding molecule-component complexes--.

Signed and Sealed this

Fourteenth Day of October, 1997

Attest:

BRUCE LEHMAN

*Attesting Officer*   Commissioner of Patents and Trademarks